(12) United States Patent
Dalton et al.

(10) Patent No.: US 9,101,401 B2
(45) Date of Patent: Aug. 11, 2015

(54) BONE REPAIR DEVICE AND METHOD

(75) Inventors: Brian E. Dalton, Erie, PA (US); Charlie Wing, Center Valley, PA (US); John Nawarynski, Allentown, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 1676 days.

(21) Appl. No.: 11/602,138

(22) Filed: Nov. 20, 2006

(65) Prior Publication Data

US 2008/0119852 A1 May 22, 2008

(51) Int. Cl.
*A61B 17/70* (2006.01)
*A61B 19/00* (2006.01)

(52) U.S. Cl.
CPC ........... *A61B 17/7032* (2013.01); *A61B 17/708* (2013.01); *A61B 17/7037* (2013.01); *A61B 17/7091* (2013.01); *A61B 2019/307* (2013.01)

(58) Field of Classification Search
USPC ................ 606/86 A, 86 R, 99–100, 246, 279, 606/264–278
See application file for complete search history.

(56) References Cited

U.S. PATENT DOCUMENTS

| | | | |
|---|---|---|---|
| 5,536,268 | A | 7/1996 | Griss et al. |
| 5,672,176 | A | 9/1997 | Biedermann et al. |
| 5,782,833 | A | 7/1998 | Haider |
| 5,810,816 | A | 9/1998 | Roussouly et al. |
| 6,740,086 | B2 | 5/2004 | Richelsoph |
| 6,858,030 | B2 | 2/2005 | Martin et al. |
| 7,491,218 | B2 * | 2/2009 | Landry et al. ................. 606/246 |
| 2004/0172022 | A1 * | 9/2004 | Landry et al. ................... 606/61 |
| 2004/0236330 | A1 | 11/2004 | Purcell et al. |
| 2004/0267264 | A1 | 12/2004 | Konieczynski et al. |
| 2004/0267275 | A1 * | 12/2004 | Cournoyer et al. ............. 606/99 |
| 2005/0033299 | A1 * | 2/2005 | Shluzas ........................... 606/61 |
| 2005/0131408 | A1 * | 6/2005 | Sicvol et al. .................... 606/61 |
| 2005/0137593 | A1 * | 6/2005 | Gray et al. ....................... 606/61 |
| 2005/0245928 | A1 * | 11/2005 | Colleran et al. ................ 606/61 |

(Continued)

FOREIGN PATENT DOCUMENTS

DE 41 27 303 C2 2/1993
DE 19726754 2/1999

(Continued)

OTHER PUBLICATIONS

Aesculap Spine S4 Spinal System Instrumentation Guide.

(Continued)

*Primary Examiner* — Eduardo C Robert
*Assistant Examiner* — Steven Cotroneo
(74) *Attorney, Agent, or Firm* — RatnerPrestia

(57) ABSTRACT

An assembly for treating a spinal disorder includes a sleeve having a socket end, a tool-receiving end and a wall extending between the socket end and tool-receiving end. The socket end has a socket opening for receiving a bone fixation screw cap and a pair of opposing notches for accommodating an elongated fixation member. A sleeve wall forms a bore extending axially between the tool-receiving end and the socket end of the sleeve. A method for repairing a spinal disorder includes the step of inserting a polyaxial screw into a vertebral bone, where the polyaxial screw has a screw cap. An elongated fixation member is inserted into the screw cap, followed by a fastener which is inserted into the screw cap in proximity to the fixation member. An adjustment device is connected to the screw cap to adjust the position of the polyaxial screw and vertebral bone.

23 Claims, 14 Drawing Sheets

(56) References Cited

U.S. PATENT DOCUMENTS

| | | | |
|---|---|---|---|
| 2006/0074418 A1* | 4/2006 | Jackson | 606/61 |
| 2006/0079909 A1* | 4/2006 | Runco et al. | 606/99 |
| 2006/0200132 A1* | 9/2006 | Chao et al. | 606/61 |
| 2007/0149980 A1* | 6/2007 | Seedhom et al. | 606/99 |

FOREIGN PATENT DOCUMENTS

| | | |
|---|---|---|
| EP | 0528177 | 2/1993 |
| EP | 1090595 | 4/2001 |

OTHER PUBLICATIONS

Aesculap Socon SRI Spondylolisthesis Reduction Instrument The Finer Points, Jeffrey Kozak, MD, 2002.

\* cited by examiner

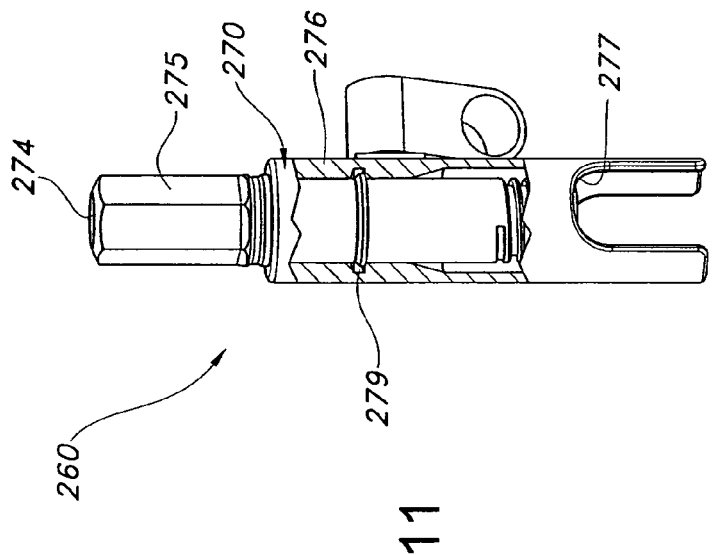
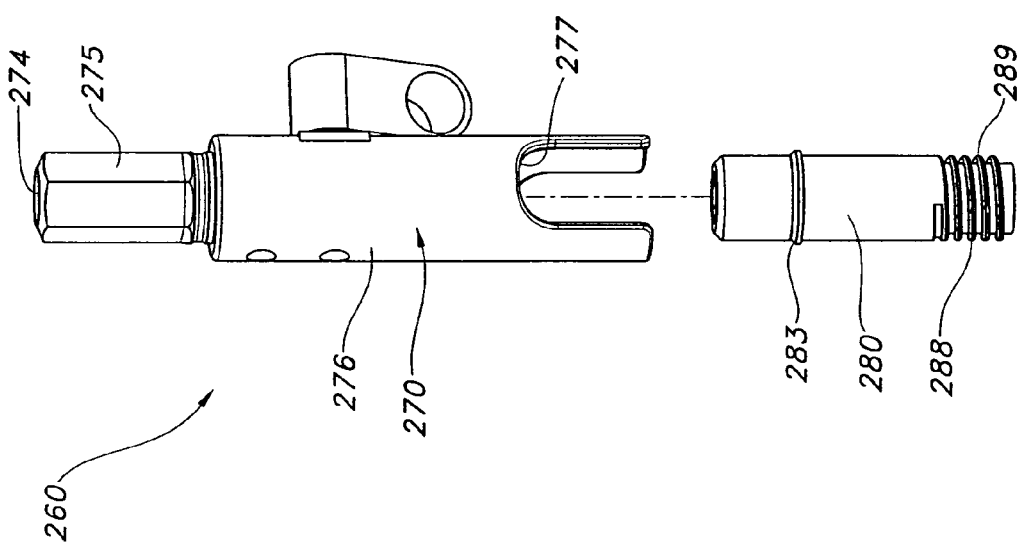
FIG. 11
FIG. 12

BONE REPAIR DEVICE AND METHOD

FIELD OF THE INVENTION

The present invention relates generally to devices for treating spinal disorders, and particularly to an apparatus and method for securing a spine rod to a patient's spine.

BACKGROUND OF THE INVENTION

The spinal column is a highly complex system of bones and connective tissues that provides support for the body and protects the delicate spinal cord and nerves. The spinal column includes a series of vertebrae stacked one atop the other, each vertebral body including an inner or central portion of relatively weak cancellous bone and an outer portion of relatively strong cortical bone. Situated between each vertebral body is an intervertebral disc that cushions and dampens compressive forces experienced by the spinal column. A vertebral canal containing the spinal cord and nerves is located behind the vertebral bodies.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease or trauma, such as ruptured or slipped discs, degenerative disc disease, fractured vertebra, and the like. Patients that suffer from such conditions usually experience extreme and debilitating pain, as well as diminished nerve function.

An exemplary spinal treatment for some of the above problems involves a technique known as spinal fixation. In spinal fixation, surgical implants are used for fusing together and/or mechanically immobilizing vertebrae of the spine. Spinal fixation may also be used to alter the alignment of adjacent vertebrae relative to one another so as to change the overall alignment of the spine. The spine may be immobilized by using orthopedic rods, commonly referred to as spine rods, that run generally parallel to the spine. This may be accomplished by exposing the spine posteriorly and fastening bone screws to the pedicles of the appropriate vertebrae. The pedicle screws are generally placed two per vertebra and serve as anchor points for the spine rods. Clamping elements adapted for receiving a spine rod therethrough are then used to join the spine rods to the screws. The aligning influence of the rods forces the spine to conform to a more desirable shape. In certain instances, the spine rods may be bent to achieve the desired curvature of the spinal column.

A number of apparatuses, sometimes referred to as jig assemblies, are used to adjust the position and orientation of the vertebra and their respective spine rods prior to setting the spine rod in the desired final position. Known jig assemblies are typically connected to the pedicle screws and around the rod in order to adjust the position of the rod and vertebra. During the adjustment process, the rod is firmly engaged against the pedicle screws so that the screws and vertebra move in an articulating relationship with the positional adjustment of the rod. Most jigs have one or more components that can lock the rod in a fixed position. Once the adjustment procedure is completed and the rod is set in a desired position, the rod is tightened against the pedicle screws to fix the screws and their respective vertebra in the desired position. To facilitate access to the rod for tightening, the typical jig assembly must be removed from the screws. This has the disadvantage of leaving the rod temporarily unsecured and unrestrained, potentially allowing the rod and vertebra to shift out of the set position. In addition, this methodology requires a number of steps, including the step of removing the jig from the screws prior to tightening the rod. Therefore, known jig assemblies have certain characteristics that may be undesirable for spinal reduction procedures.

SUMMARY OF THE INVENTION

The drawbacks of known jig assemblies and individual components used with jig assemblies are resolved to a large degree by the present invention. In a first embodiment of the invention, an assembly for treating a spinal disorder includes a generally cylindrical sleeve having a socket end, a tool-receiving end and a wall extending between the socket end and tool-receiving end. The socket end has a socket opening for receiving a bone fixation screw cap and a pair of opposing notches for accommodating an elongated fixation member associated with the bone fixation screw cap. A sleeve wall forms a hollow bore extending axially between the tool-receiving end and the socket end of the sleeve.

In a second embodiment of the invention, an assembly for treating a spinal disorder includes an outer sleeve having a bore, and a locking sleeve disposed within the bore. The outer sleeve includes a socket end and a tool-receiving end. The bore extends axially between the socket end and tool-receiving end. The socket end has a socket opening for receiving a bone fixation screw cap in the bore. The locking sleeve includes a tool-engaging end, a mounting end, and a hollow passage extending axially between the tool-engaging end and mounting end. The mounting end has a surface for engaging a bone fixation screw cap to lock the position of the outer sleeve relative to the bone fixation screw cap.

In a third embodiment of the invention, a method for repairing a spinal disorder includes the step of inserting a polyaxial screw into a vertebral bone, where the polyaxial screw has a screw cap. An elongated fixation member is inserted into the screw cap, followed by a fastener which is inserted into the screw cap in proximity to the elongated fixation member. An adjustment device is connected to the screw cap, where the adjustment device operates to adjust the position of the polyaxial screw and vertebral bone. The position of the polyaxial screw and vertebral bone are then adjusted with the adjustment device until the vertebral bone is in a desired final position. A tool is inserted through the adjustment device to engage the fastener, and the fastener is tightened against the elongated fixation member with the tool to secure the position of the vertebral bone in the desired final position.

BRIEF DESCRIPTION OF THE DRAWINGS

The foregoing summary and the following detailed description will be better understood when read in conjunction with the following drawing figures, of which:

FIG. 11 is an exploded perspective view of components of an engagement assembly in accordance with a third embodiment of the present invention, illustrating individual components in a disassembled condition.

FIG. 12 is a perspective view of components of the engagement assembly of FIG. 11, illustrating components in a partial cut-away view to show the components in an assembled condition.

DETAILED DESCRIPTION OF THE INVENTION

The present invention generally relates to an assembly and method used to perform spinal fixation. The assembly of the present invention includes a jig apparatus that allows an orthopedic spine rod to be adjusted into a final position, held in the final position under a retention force, and secured in the final position without removal of the retention force or removal of the jig apparatus. Because the jig apparatus remains in place as the rod is secured in the final position, there is little or no risk of the vertebrae shifting out of position prior to being secured in place, because the retention force on the rod is not removed until after the rod is secured.

Figure 1:
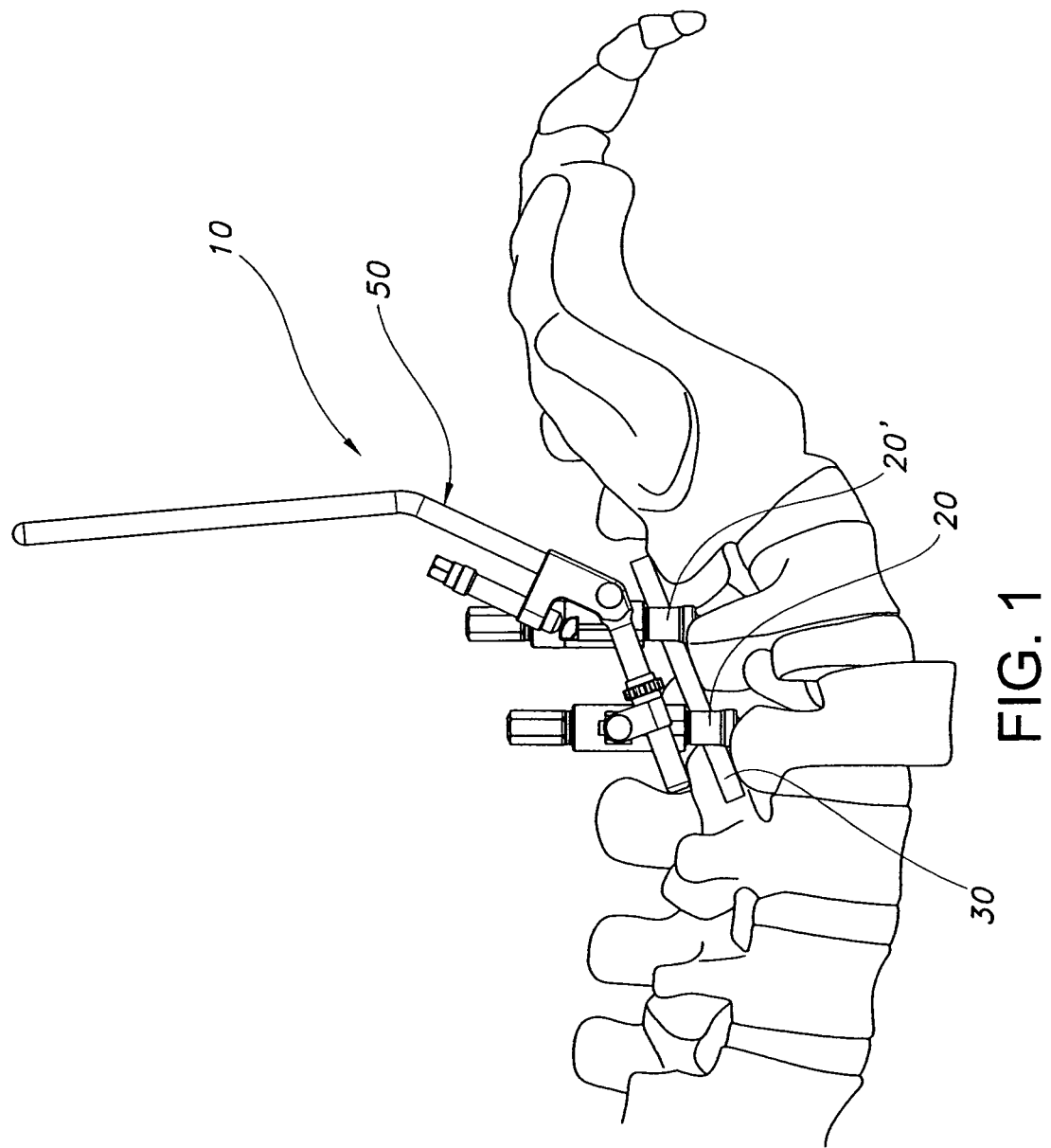
FIG. 1 is an elevation view of an apparatus in accordance with a first embodiment of the present invention, the apparatus being illustrated schematically in a spinal procedure.
Figure 2:
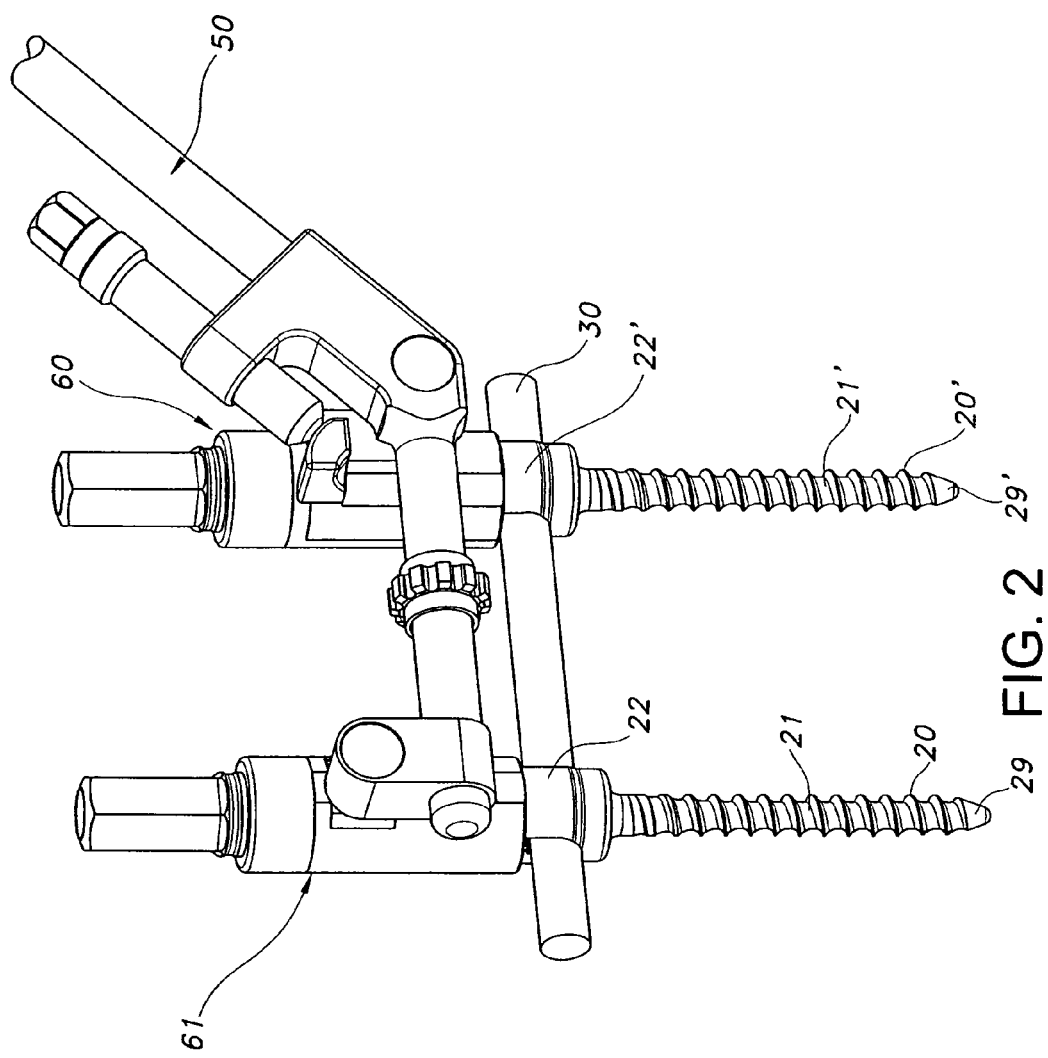
FIG. 2 is a perspective view of the apparatus shown in FIG. 1, the apparatus being shown with certain components truncated for clarity.

Referring now to the drawing figures generally, and FIGS. 1 and 2 in particular, a spondylolisthesis reduction assembly 10 in accordance with a first embodiment of the present invention is shown. It should be understood that multiple assemblies having configurations as shown in FIG. 1, or other configurations, may be used in a given procedure. The arrangements illustrated herein are intended only for purposes of illustrating possible configurations. Assembly 10 includes two bone fixation screws 20 and 20' and an adjustment apparatus or jig 50. Bone screw 20 is screwed into a vertebral body 4 to be repositioned, and bone screw 20' is screwed into an adjacent vertebral body 6. Screws 20 and 20' collectively anchor and support an elongated fixation member, which is shown as a cylindrical rod 30. Rod 30 exerts forces on the vertebra to alter the shape of the spine. It will be understood that in surgical procedures, the rod may span three or more vertebra. For purposes of clarity, however, rod 30 is shown in shortened form so as to span only two vertebra.

Figure 3:
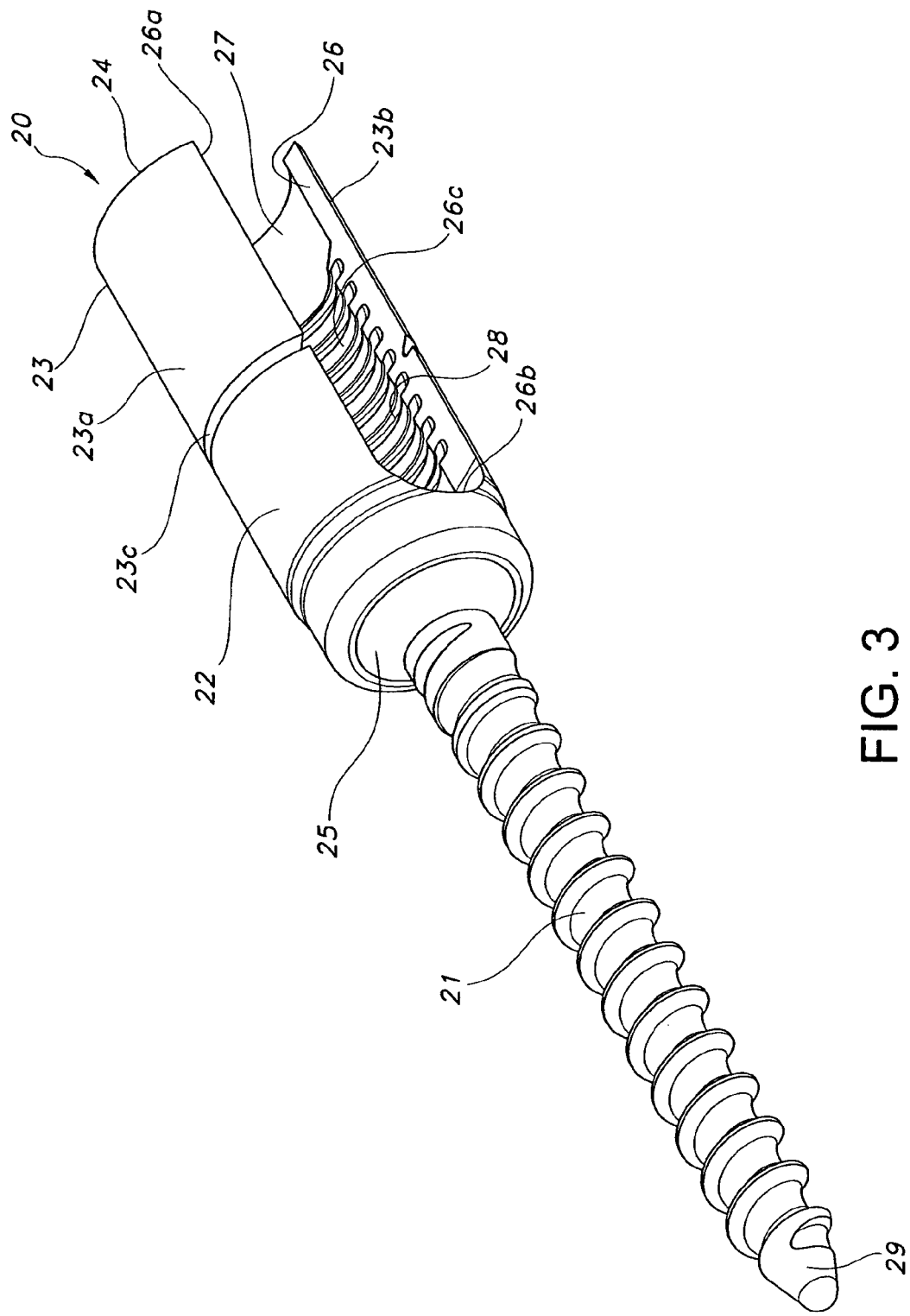
FIG. 3 is a perspective view of a pedicle screw used with the apparatus shown in FIG. 1.

The components of the assembly 10 will be described in greater detail. Screws 20 and 20' are identically configured. For purposes of this description, the features of screw 20 will be described, with identical features of screw 20' being identified in the drawing figures with the same number followed by a prime symbol ('). Referring to FIG. 3, screw 20 has a threaded shank 21 with a pointed end 29 that can be driven into a vertebral body to fix the position of the screw relative to the vertebral body. Screw 20 also includes a generally cylindrical screw cap 22 that circumscribes an end of the screw opposite the pointed end. Screw cap 22 includes a cylindrical wall 23 having a proximal end 24, which is open, and a distal end 25, which circumscribes screw 20.

Screw cap 22 serves as a base or support point for anchoring a section of rod 30. Cylindrical wall 23 is hollow and forms an interior longitudinal passage 27. A pair of opposing slots 26 extend longitudinally along the cylindrical wall 23. Each slot 26 has an open end 26a adjacent proximal end 24 of wall 23, and a rounded end 26b. The diametrically opposing slots 26 are spaced approximately 180 degrees from one another in a symmetrical arrangement on the circular perimeter of cylindrical wall 23. In this arrangement, the slots 26 align with one another to form a conduit 26c through the screw cap that extends transversely to the longitudinal or axial passage 27. The conduit 26c has a width that is slightly greater than the diameter of the rod 30, allowing rod 30 to be inserted through conduit 26c to connect the rod with the screw cap 22.

The radius of curvature of rounded end 26b in slot 26 generally conforms to the curvature of rod 30. Preferably, the radius of curvature of rounded end 26b is equal to or slightly larger than the radius of curvature of rod 30. In this arrangement, rod 30 may be cradled and supported in the screw cap 22 in a stable and secure position, with resistance to lateral movement in a direction transverse to the slots 26. Rod 30 may be flexible to permit bending and flexion of the rod in a direction parallel to the slots 26, however. Therefore, slots 26 provide a guide to control the axial position of the rod with respect to the longitudinal axis of pedicle screw cap 22, while limiting lateral displacement.

In the embodiment illustrated thus far, screw cap 22 has been illustrated with an elongated cylindrical wall 23. Although the length of wall 23 need not be particularly long, it is preferred that the wall be relatively long to provide a sufficiently long base on which to mount the jig 50. This arrangement provides more stability to the jig 50 when the jig is connected over the screw caps 22.

The inner passage 27 of screw cap 22 includes an engagement surface for receiving a fastener. The screw cap 22 cooperates with the fastener to secure the rod within conduit 26c of the screw cap. A variety of engagement surfaces and fasteners may be used to secure the rod 30 within the screw cap 22. For example, a pin may be inserted though a hole in the side of the screw cap after the rod is seated to prevent the rod 30 from moving out of the screw cap.

Figure 4:
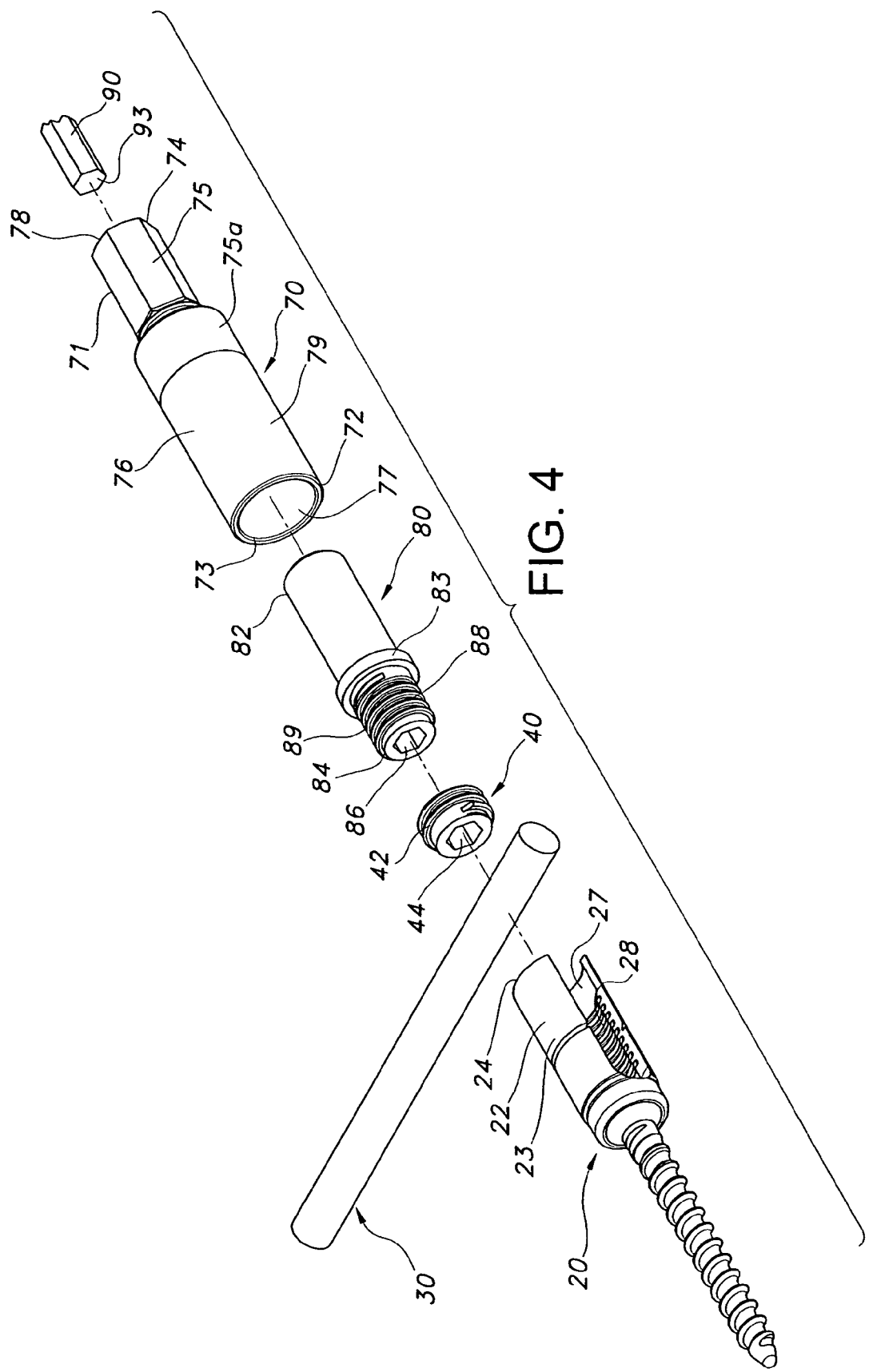
FIG. 4 is an exploded perspective view of components shown in FIG. 1, in conjunction with a spine rod and torque-applying tool in accordance with the present invention.

Referring to FIG. 4, a fastener in the form of a set screw 40 secures the rod 30 within screw cap 22. Set screw 40 has a generally circular or disc shape with an external thread 42 on its outer circumference. The inside of cylindrical wall 23 in screw cap 22 has a corresponding internal thread 28. The external thread 42 of set screw 40 cooperatively engages internal thread 28 on the cylindrical wall 23 to facilitate axial displacement of the set screw in the passage 27 when the set screw is inserted in the screw cap 22 and rotated. Preferably, the threads 28 and 42 are arranged so that set screw 40 advances distally, or toward the rounded ends 26b of slots 26, in response to clockwise rotation, and proximally, or away from the rounded ends 26b of slots 26, in response to counterclockwise rotation. Set screw 40 includes a hole 44 having a shape and depth that mate with a torque applying tool. Hole 44 may have a variety of conventional shapes and configurations, including but not limited to a hole adapted to engage an Allen wrench, Philips head screwdriver, or other conventional torque applying tool.

Figure 5:
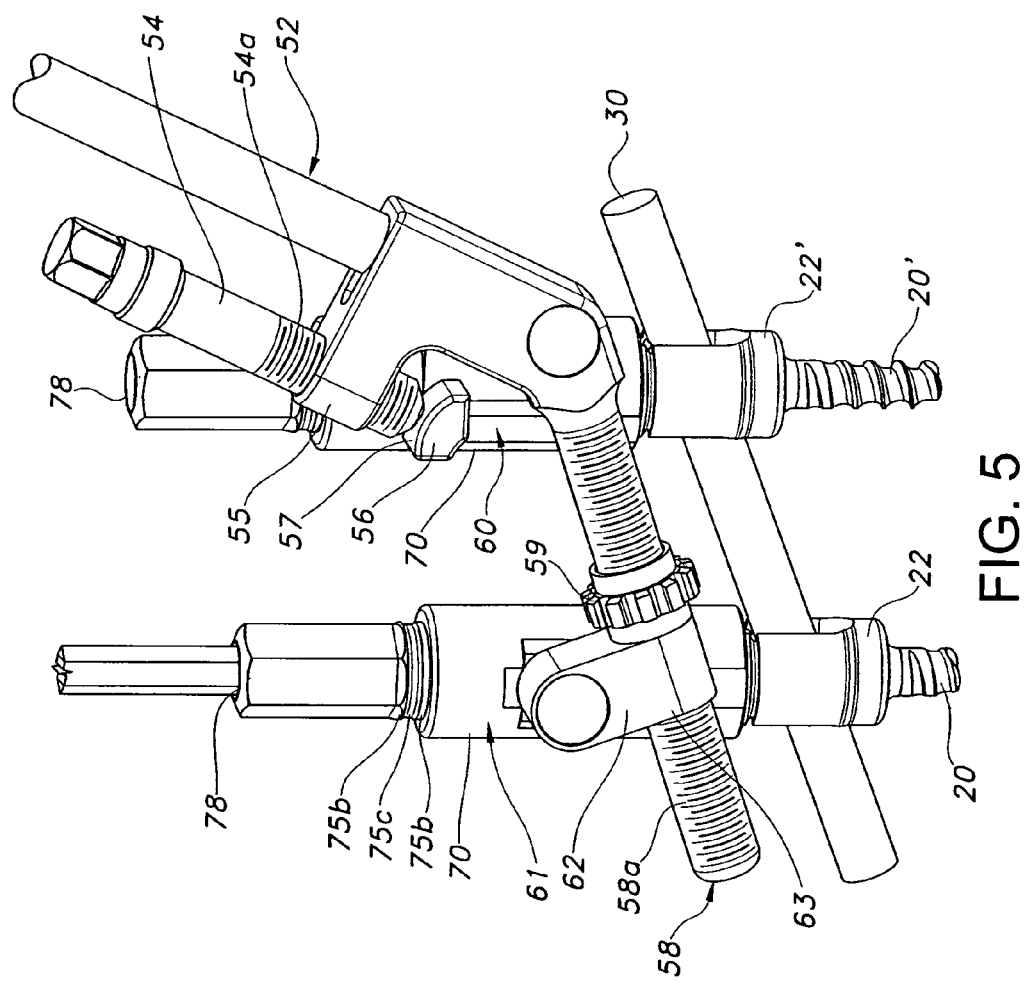
FIG. 5 is a partially-truncated perspective view of the apparatus shown in FIG. 1, shown in a partial cut-away view to illustrate components of the apparatus.

The position and influence of the rod 30 are controlled by the adjustment apparatus or jig 50. Jig 50 is operable to incrementally adjust the position of rod 30, apply a retaining force on the rod between incremental adjustments, and facilitate securement of the rod in a final position without removing the retaining force. Referring to FIGS. 2 and 5, jig 50 includes a first engagement member 60 and a second engagement member 61, each of which connects with a screw cap associated with a pedicle screw. First engagement member 60 is positioned adjacent to a lever or handle portion 52. Second engagement member 61 is offset or spaced apart from first engagement member 60, and includes a bearing sleeve 62. A strut 58 extends from handle portion 52 and into a bore 63 in bearing sleeve 62. Handle portion 52 and strut 58 are pivotally connected to the first engagement member 60 at a pivot point. As such, first and second engagement members 60 and 61 are interconnected with one another and with handle portion 52 in an articulating arrangement. The relative positions of screw caps 22 and 22' can be adjusted in response to forces applied to handle portion 52. More specifically, the position of screw cap 22 relative to screw cap 22' can be adjusted with respect to at least two different axes.

As noted above, jig 50 is operable to incrementally adjust the position of rod 30. Once rod 30 is adjusted to a desired position, jig 50 is operable to lock or retain the rod in the desired position, so that the rod is immobilized until fasteners 40 can be tightened to secure the rod in place. Engagement member 60 includes a mechanism for immobilizing the position of rod 30 during the adjustment procedure. Referring to FIG. 5, the locking mechanism is illustrated in the form of a stop 56 having a curved surface 57. The curved surface 57 cooperatively engages a generally cylindrical adjusting arm 54 that is coupled with handle portion 52. Adjusting arm 54 extends through a sleeve 55 coupled with handle portion 52. Adjusting arm 54 is axially displaceable through the sleeve 55 to abut the curved surface 57 on stop 56. In a preferred embodiment, arm 54 has a plurality of external threads 54a that engage internal threads in the sleeve 55 so that the adjusting arm axially advances through the sleeve upon rotation. Arm 54 is displaceable between an unlocked condition, in which the arm is spaced apart from the curved surface 57 of stop 56, and a locked condition, in which the arm contacts the curved surface. In the locked condition, arm 54 substantially prevents pivoting of the handle portion 52 relative to engagement member 60.

Engagement member 61 also includes a mechanism for immobilizing the position of rod 30 during the adjustment procedure. In FIG. 5, the locking mechanism is illustrated in the form of a knurled nut 59 that circumscribes the strut 58. Strut 58 includes a series of external threads 58a that engage a series of internal threads in the knurled nut. Knurled nut 59 is axially displaceable on strut 58 upon rotation of the knurled nut. In this arrangement, knurled nut 59 is displaceable between an unlocked position, in which the nut is spaced apart from bearing sleeve 62, and a locked position, in which the nut abuts the bearing sleeve. In the locked position, further axial advancement of nut 59 in the direction of bearing sleeve 62 is prevented. The engagement of nut 59 and bearing sleeve 62, combined with the abutment of adjusting arm 54 and stop 56, retain rod 30 in an immobilized condition and prevent the rod and pedicle screws 20 and 20' from shifting out of the set position while the rod is secured in the screw caps 22 and 22'.

Figure 6:
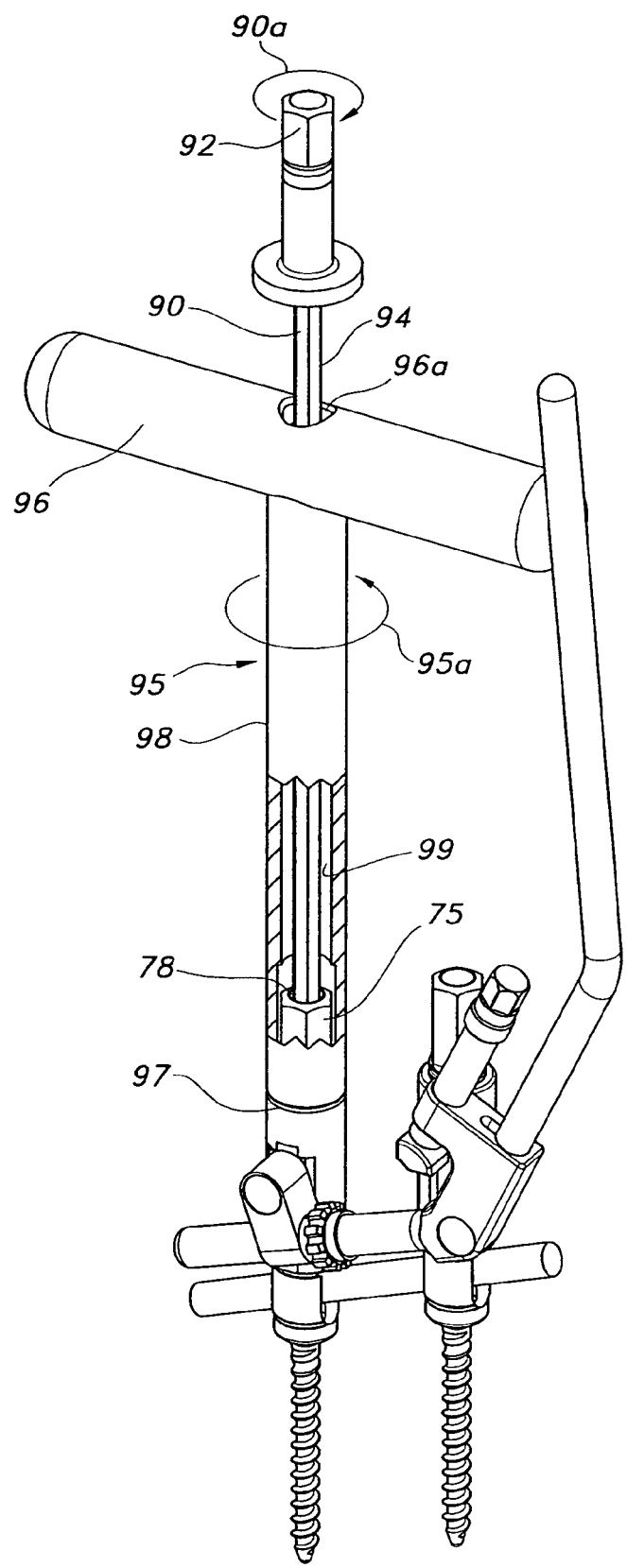
FIG. 6 is a truncated perspective view of the apparatus shown in FIG. 1, the apparatus being shown schematically in use with torque-applying tools in accordance with the present invention, where components of the apparatus are shown in a partial cut-away view.

Referring to FIGS. 4-6, the engagement members include an elongated outer sleeve 70 having a socket end 72, a tool-engaging end 74 and a generally cylindrical wall 76 that extends between the socket end and tool-receiving end. Outer sleeve 70 is generally hollow and forms a bore 77 that extends the length of the sleeve from the socket end 72 to the tool-engaging end 74. Socket end 72 includes a socket opening 73 in communication with bore 77. Socket opening 73 has a diameter that is slightly larger than the outer diameter of screw caps 22 and 22'. In this arrangement, the socket opening 73 on each engagement member receives a screw cap to connect the jig 50 to the screw cap. The axis of bore 77 is positioned generally in coaxial alignment with the center axis of the passage 27 in the screw cap.

The tool-engaging end 74 and bore 77 in outer sleeve 70 are adapted to receive the end of an Allen wrench or other torque applying implement. Bore 77 acts an access port for the torque applying implement and facilitates access to the hole 44 in set screw 40 so that the set screw can be advanced in the axial passage 27 of a screw cap. In FIGS. 5 and 6, a torque applying tool in the form of an Allen-type wrench 90 is inserted through the tool-engaging end 74 of outer sleeve 70. As will be explained in more detail, wrench 90 is operable to engage the set screw 40 through the outer sleeve of jig 50 to tighten down the rod 30 in a fixed position.

Referring again to FIG. 4, outer sleeve 70 includes a head portion 71 and a body portion 79. Head portion 71 includes a hex head 75 and a collar 75a that circumscribes the hex head. Hex head 75 is rotatably mounted in the collar 75a. An inner locking sleeve 80 is axially displaceable in the bore 77 of each outer sleeve 70. Locking sleeve 80 is operable to tighten the outer sleeve 70 onto a screw cap to secure the jig 50 to the associated pedicle screw. Locking sleeve 80 includes a proximal mounting end 82 and a distal mounting end 84. A variety of mounting end configurations may be used. In the illustrated embodiment, the proximal mounting end 82 is shown in the form of a substantially flat end. Proximal mounting end connects with a distal end of hex head 75 inside collar 75a. Hex head 75 and locking sleeve 80 may be interconnected in a number of ways, including but not limited to a welded connection or a threaded engagement where the proximal mounting end 82 of locking sleeve 80 is threaded into the bore of the hex head. In this arrangement, locking sleeve 80 and the hex head 75 portion of outer sleeve 70 are integrally connected and rotatable in unison with respect to the outer sleeve 70 in response to torque applied to the hex head.

Hex head 75 includes a tool opening 78 sized to receive the end of a first torque-applying tool, such as wrench 90. In addition, hex head 75 includes a hexagonal-shaped perimeter to engage a second torque-applying tool, such as a socket wrench. As explained in more detail below, the perimeter of hex head 75 may be engaged with a socket wrench to apply a counter-torque during tightening of the set screw 40.

The size and configuration of the hex head may be varied, depending on a number of variables including but not limited to the type of torque-applying tool used. In the preferred embodiment, outer sleeve 70 includes an elongated hex head, an example of which is shown by hex head 75 in FIG. 4. Hex head 75 cooperates with a standard-sized socket wrench attachment. The longer length of hex head 75 ensures a secure connection with the socket fitting. A pair of ridges 75b extend circumferentially around the perimeter of hex head 75, forming a recess portion or groove 75c between the ridges 75b. The ridges 75b and groove 75c cooperate with the end of a socket wrench to securely grip the socket in frictional engagement. As an alternative to the elongated hex head 75, a shorter hex head may be selected for applications where open wrenches, box wrenches, or other torque-applying tools requiring less surface contact with the hex head are used.

Locking sleeve 80 is configured for insertion in bore 77 in an axial position above set screw 40. A round hollow passage 86 extends though the locking sleeve 80 between the proximal mounting end 82 and distal mounting end 84. Passage 86 extends in a generally coaxial relationship with bore 77 in the outer sleeve 70 and in a generally coaxial relationship with hole 44 in set screw 40. In this aligned condition, passage 86 allows a tool inserted through the tool-receiving end 74 of the outer sleeve 70 to pass through the locking sleeve 80 and engage the set screw 40.

The distal mounting end 84 of locking sleeve 80 has an outer diameter that is slightly less than the inner diameter of axial passage 27 of screw cap 22. In this configuration, axial passage 27 is adapted to receive the distal mounting end 84 of locking sleeve 80. Locking sleeve 80 includes a locking surface 88 for tightening down the outer sleeve 70 on screw cap 22. A variety of different mechanisms may be used for interconnecting the locking sleeve 80 with the screw cap 22. For example, the locking surface 88 illustrated in FIG. 4 includes an external thread 89 that engages the inner thread 28 which extends along the wall 23 of screw cap 22. In this arrangement, locking sleeve 80 operates much like a bolt by being axially displaceable in passage 27 in response to torque applied to the locking sleeve. Locking sleeve 80 may be rotated by applying torque to the hex head 75, as noted above. In the preferred embodiment, locking sleeve 80 advances in the screw cap toward the rod 30 in response to clockwise rotation, and advances in the screw cap away from the rod in response to counter-clockwise rotation.

A flange 83 extends radially outwardly from a section of the locking sleeve 80 above the external thread 89. The diameter of the flange 83 is preferably equal to or substantially equal to the diameter of bore 77 in outer sleeve 70 so that the flange frictionally engages the inside wall surrounding bore 77 as the locking sleeve is advanced through the outer sleeve. This arrangement maintains the locking sleeve 80 in a substantially centered and axially aligned position in the bore 77, i.e. a position in which the passage 86 through locking sleeve 80 remains substantially coaxial with the axis of the bore 77 in the outer sleeve 70. The diameter of flange 83 is greater than the inner diameter of screw cap 22, such that the flange can not enter into axial passage 27 in the screw cap. Locking sleeve 80 is axially displaceable in the passage 27 to a bottomed-out position in which the flange 83 abuts the proximal end 24 of screw cap 22.

The manner in which the engagement members are tightened into pedicle screws will now be described. Engagement member 60 (or 61) is assembled with the locking sleeve 80 positioned inside the outer sleeve 70. Locking sleeve 80 is disposed in the outer sleeve 70 so that the locking sleeve can rotate independently relative to the outer sleeve, but cannot move axially relative to the outer sleeve. Outer sleeve 70 is positioned over the proximal end 24 of a screw cap 22 extending from an implanted pedicle screw. The socket opening 73 of outer sleeve 70 is aligned over the cylindrical wall 23 of screw cap 22 and pushed down over the screw cap. As the outer sleeve 70 is moved down over the screw cap 22, distal mounting end 84 of locking sleeve 80 enters axial passage 27 in the screw cap until the external thread on the distal mounting end engages the inner thread in the screw cap.

The distal mounting end 84 is advanced further into the screw cap 22 by applying a clockwise torque to the hex head 75. Locking sleeve 80 rotates in response to the clockwise torque applied to the hex head 75, and the external thread on distal mounting end 84 engages the inner thread 28 in screw cap 22 to draw the distal mounting end further into the screw cap. Rotation of the locking sleeve 70 advances the locking sleeve downwardly (i.e. toward the pedicle screw), which in turn pulls the hex head 75 downwardly. The dimensions of hex head 75 are sufficiently large in comparison to the dimensions of collar 75*a* that the hex head cannot pass through the collar. Distal mounting end 84 advances axially into screw cap 22 until flange 83 engages the proximal end 24 of screw cap 22, at which time the outer sleeve 70 and locking sleeve 80 can not advance any further relative to the screw cap 22. Additional torque applied to the hex head 75 will create tensile forces between the locking sleeve 80 and screw cap 22 to tighten the engagement between the engagement member and the screw cap.

The manner in which rod 30 is secured in place will now be described. The engagement members 60 and 61 are advanced over screw caps 22 and 22' and tightened in accordance with the procedure described previously. When rod 30 is set in a desired position, the adjusting arm 54 and knurled nut 59 are moved to the locked condition to immobilize the jig 50 and rod. An Allen wrench 90 or comparable torque applying tool is inserted into tool opening 78 of outer sleeve 70 and advanced through the hex head 75 and locking sleeve 80 until the end of the tool engages the hex hole 44 in set screw 40. Wrench 90 includes a handle engaging end 92, a fastener engaging end 93 and a shaft 94 extending between the handle engaging end and fastener engaging end. A number of different handles or levers may be attached to handle engaging end 92 to operate torque wrench 90. Fastener engaging end 93 is configured to engage the hex hole 44 of set screw 40 and transfer torque to the set screw.

A clockwise torque is applied to wrench 90, as illustrated by arrow 90*a* in FIG. 6, to rotate the set screw 40 and axially advance the set screw toward rod 30. Set screw 40 is rotated until it contacts the rod 30, at which time further rotation will create tensile forces between threads 42 on the screw and threads 28 in the screw cap 22. These tensile forces hold the set screw 40 against rod 30 in a tight engagement to secure the rod in the desired position.

Advancement of the set screw 40 into the passage 27 of screw cap 22 exerts radial forces outwardly against the cylindrical wall 23. Because the slots 26 extend along a substantial portion of cylindrical wall 23, portions of the wall between the slots form cantilevers that are prone to a certain amount of outward deflection. These cantilever portions of wall 23, if left unrestrained, could deflect outwardly in response to the radial forces that are exerted as the set screw is driven into passage 27 of screw cap 22. Deflection of the wall 23 can cause the inner thread 28 along inner passage 27 to move out of alignment with the external thread 42 on set screw 40, leading to slippage of the set screw. The outer sleeve 70 prevents movement of the threads 28 during the advancement of the set screw by forming a circumferential restraint around the cylindrical wall 23. The circumferential restraint keeps the cylindrical wall 23 from deflecting outwardly in response to radial forces exerted during advancement of the set screw 40.

If desired, a socket wrench may be engaged with the hex head 75 to apply a counter-torque on the hex head and locking sleeve 80 while clockwise torque is being applied to rotate the set screw. This minimizes the potential for inadvertent rotation of the locking sleeve, screw cap or other components that tightly engage the locking sleeve. The counter-torque applied to the locking sleeve 80 transfers to screw cap 22 to balance any clockwise torque that transfers from the set screw 40 to the screw cap.

Referring to FIG. 6, a tool assembly includes a torque wrench 90 inserted through a counter-torque wrench 95. Torque wrench 90 and counter-torque wrench 95 are operable to simultaneously tighten the set screw 40 while minimizing deflection or deformation of the screw cap 22 in response to torque transferred from the tightening of the set screw. As noted above, torque wrench 90 is operable to apply a clockwise torque, shown by arrow 90*a*, to tighten set screw 40 in screw cap 22.

Counter-torque wrench 95 is operable to apply a balancing counter-clockwise torque, as shown by arrow 95*a*. Counter-torque wrench 95 has a handle 96, a socket end 97, and a cannulated or hollow body 98 that extends between the handle and socket end. Socket end 97 is adapted to receive hex head 75 of outer sleeve 70. Handle 96 has a T-shaped handle end with an opening 96*a* that connects with the interior of hollow body 98. Hollow body 98 forms an interior access way 99 adapted to receive torque wrench 90. The handle opening 96*a* provides a portal into access way 99 to permit torque wrench 90 to be inserted through the hollow body of counter-torque wrench 95. In this arrangement, the torque wrench 90 and counter-torque wrench 95 may be engaged with the jig 50 at the same time and operated to simultaneously apply a clockwise torque to set screw 40 and a counter-clockwise torque to the hex head 75.

In some instances, a section of rod 30 will be suspended in a slot 26 of screw cap 22, above the rounded end 26*b* in the slot. For example, if rod 30 is secured at an inclined angle, as shown FIG. 1, one or more sections of the rod may be held down by the set screw 40 in a position in which the rod is seated at a tilted angle. The rod may be seated against the round end 26*b* of one slot 26 in a screw cap 22, while raised above the round end 26*b* of the opposite slot in the screw cap. In such instances, cylindrical wall 23 and slots 26 need to have sufficient lengths to enclose the rod in the tilted orientation. In other cases, rod 30 may be seated at the bottom of slot 26 against rounded end 26*b*. The length of cylindrical wall 23 need not be as long in such instances, because the rod 30 is contained within the lower portion of screw cap 22.

In view of the different rod positions that are contemplated by the present invention, it is desirable to provide components that allow the length of the screw cap 22 to be adjusted in accordance with how much of the slot is occupied by rod 30. Preferably, the length of cylindrical wall 23 can be selected during the rod installation procedure based on the angle of inclination that is anticipated. In particular, it would be desirable to include a mechanism for shortening the wall 23 of screw cap 22 for cases where the excess wall length is not required.

Referring back to FIG. 3, cylindrical wall 23 of screw cap 22 includes a pair of break-away tabs or sections 23*a* and 23*b*. Break-away tabs 23*a* and 23*b* allow the length of screw cap 22 to be modified in cases where the full length of wall 23 is not needed to contain the rod 30. A variety of break-away connections may be used in forming the break-away tabs, including scoring or slits cut into the wall. In FIG. 3, cylindrical wall 23 includes a thinned section 23*c* that extends around the circumference of the wall at a section located approximately midway between proximal end 24 and distal end 25 of cylindrical wall. The thinned section 23*c* forms a relatively weakened section having a low resistance to shear. In this arrangement, the proximal portion of wall 23 can be sheared off by applying a torque on the proximal portion of the wall. The resistance to shear is low enough that torque is not transferred to the distal portion of the wall 23 and pedicle screw 20.

As noted above, orthopedic rods may be connected to pedicle screws which are offset from one another in an inclined arrangement, such as the arrangement in FIG. 1. That is, the adjacent pedicle screws may be offset both vertically and horizontally from one another. In some cases, the relative position of the pedicle screws creates a relatively steep angle of inclination for the rod. For example, the rod may be positioned at an incline of 20 degrees or more relative to a plane passing through the spine. Therefore, it may be desirable to use components that permit a greater degree of rod angulation.

Figure 7:
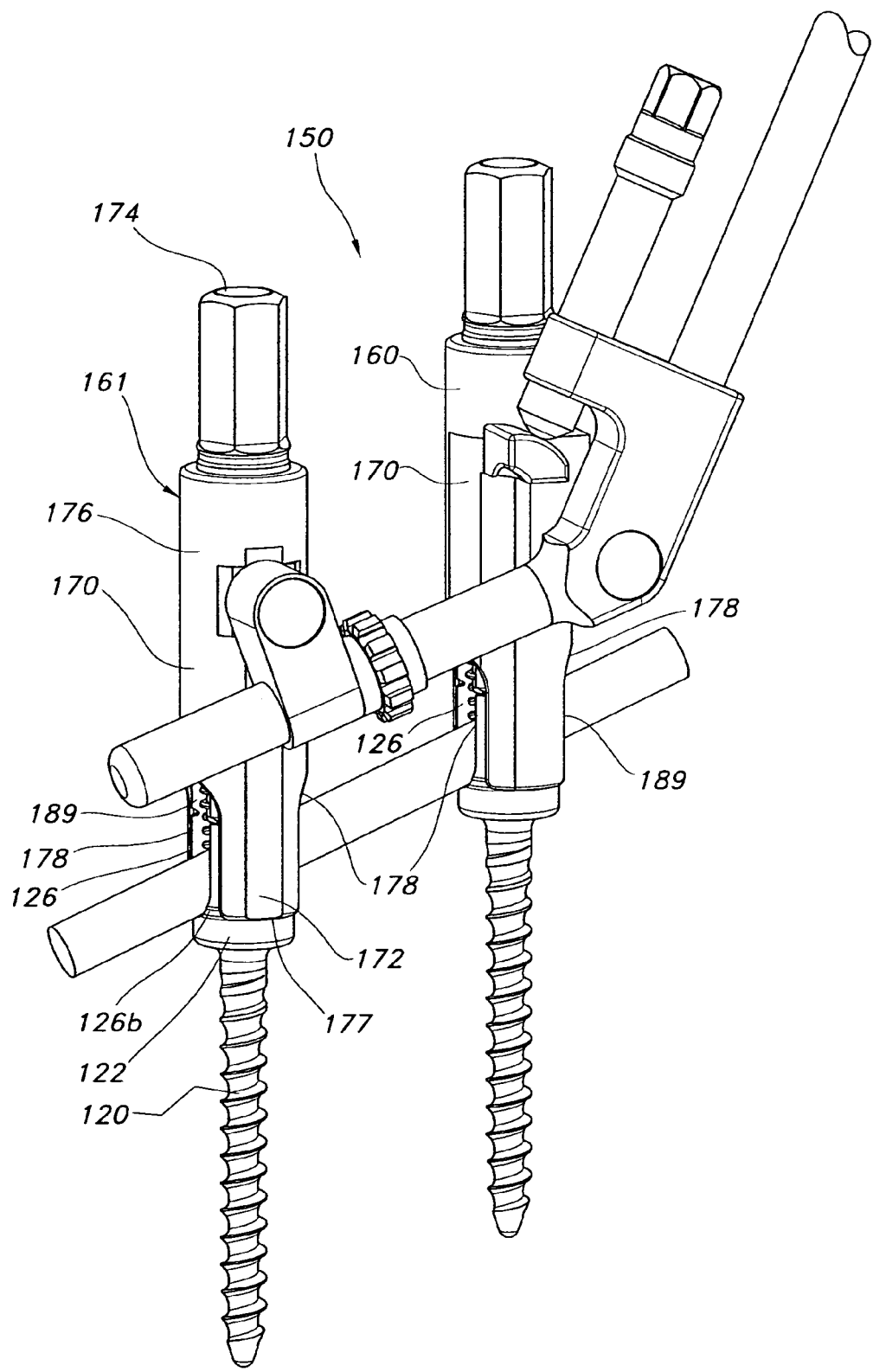
FIG. 7 is a partially-truncated perspective view of an apparatus in accordance with a second embodiment of the present invention.
Figure 8:
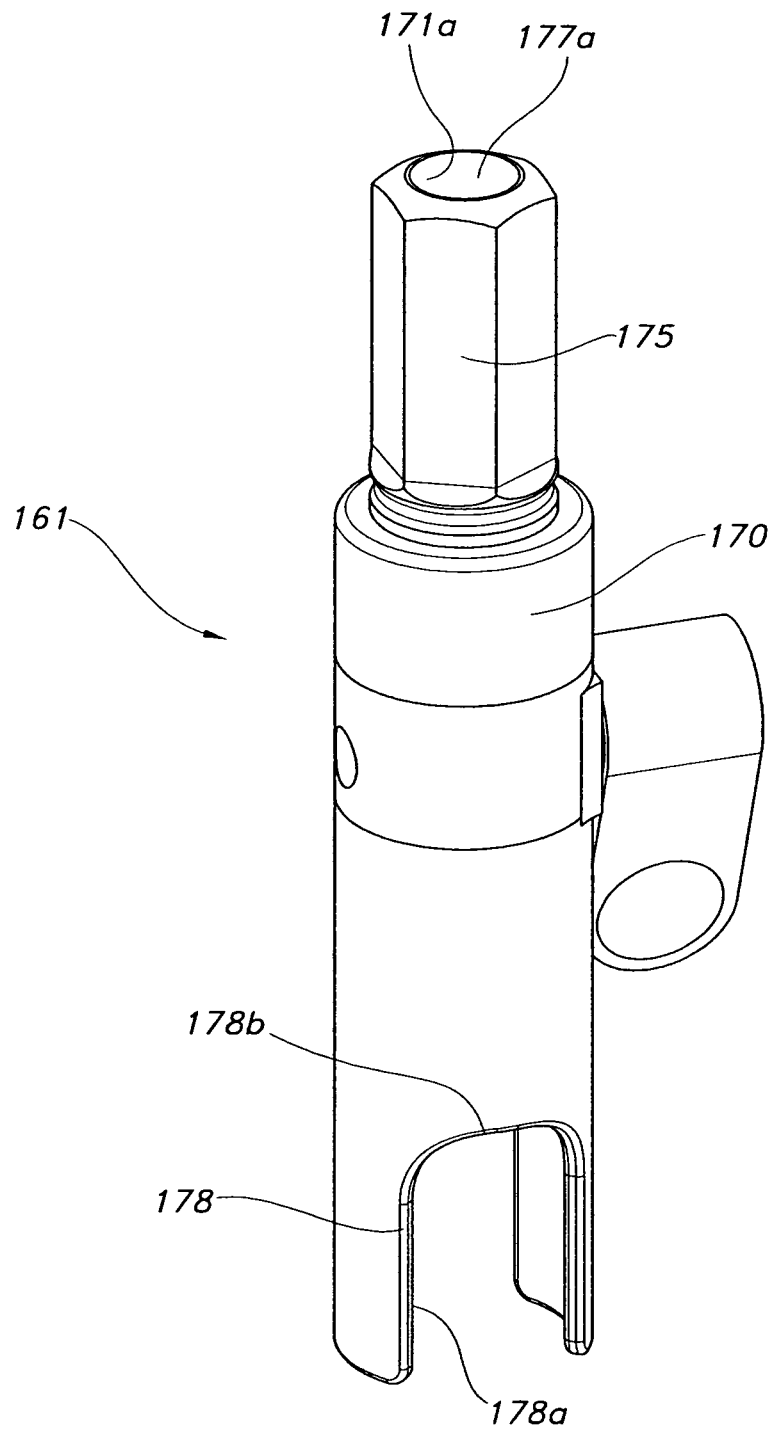
FIG. 8 is a perspective view of a component of the apparatus of FIG. 7.

Referring now to FIGS. 7 and 8, a jig assembly 150 in accordance with a second embodiment of the invention is shown. For purposes of this description, elements of jig 150 that correspond to similar elements in the first embodiment will be identified with the same reference number plus 100. Jig assembly 150 features a pair of engagement members 160 and 161, each having an outer sleeve 170 that permits a wide range of angulation. Each outer sleeve 170 includes a socket end 172, a tool engaging end 174 and a generally cylindrical wall 176 extending between the tool receiving end and the socket end. In contrast to other embodiments of the invention described previously, outer sleeve 170 has a longer cylindrical wall 176 forming a deeper bore 177 for receiving a screw cap 122 on a pedicle screw 120. The longer cylindrical wall 176 increases the stability of the jig 150 on the screw cap 122. In addition, the cylindrical wall 176 forms a longer restraint to prevent the screw cap 122 from deflecting in response to advancement of a set screw 140.

Outer sleeve 170 also includes a pair of opposing notches 178. Each notch 178 includes an open end 178*a* adjacent to the socket end 172 of sleeve 170. In addition, each notch 178 includes a rounded end 178*b* opposite the open end, the rounded end being located at a midportion of sleeve 170. Notches 178 are separated by an angle of approximately 180 degrees along the circumference of wall 176. In this arrangement, the notches 178 are adapted to generally align with slots 126 in screw cap 122 when the respective engagement member 161 is placed over the screw cap, as shown in FIG. 7.

Notches 178 and slots 126 are arranged so as to form a closed aperture 189 when the engagement member is connected over the screw cap 122. Aperture 189 is elongated with a length significantly longer than the diameter of a spinal rod. This permits the rod to move through a wider range of angles and axial positions during incremental adjustment of the rod. The aperture 189 is bounded at one end by the rounded end 126*b* of slot 126 in screw cap 122, and bounded at the opposite end by rounded end 178*b* of notch 178 in the engagement member. In this arrangement, aperture 189 has a rounded configuration at both ends which conforms with the round geometry of a spinal rod.

Figure 9:
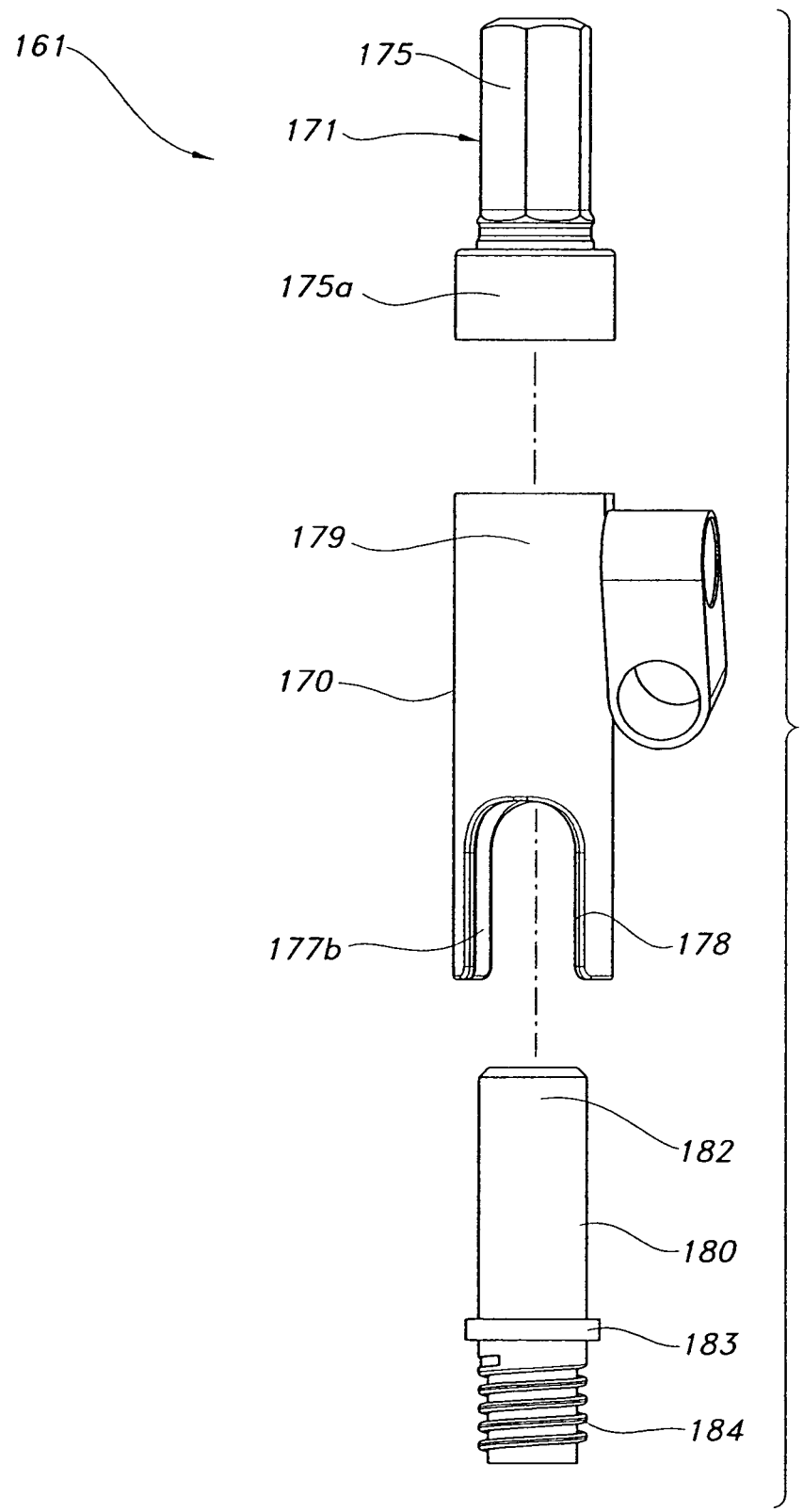
FIG. 9 is an exploded elevation view of components of the apparatus shown in FIG. 7.

The engagement member may be formed with a number of configurations, the selection of which may depend on factors including but not limited to manufacturing preferences. Referring now to FIGS. 8 and 9, an engagement member 161 includes an outer sleeve 170 and an inner locking sleeve 180 which is received in the outer sleeve. Locking sleeve 180 is slidably displaceable in outer sleeve 170 both axially and radially. Outer sleeve 170 is formed of two separate parts which function, among other purposes, to permit assembly of the outer sleeve with the inner sleeve. Outer sleeve 170 includes a head portion 171 and a body portion 179 connected to the head portion. Head portion 171 and body portion 179 may be interconnected to one another by welding or other suitable method. Head portion 171 includes a hex head 175 and a collar 175a that circumscribes the hex head 175. Hex head 175 is rotatable in the collar 175a. Referring to FIG. 9, collar 175a can be welded to a proximal end of the body portion 179 to interconnect the head portion 171 with the body portion 179. A bore 177a extends through the hex head 175 and collar 175a. Body portion 179 of outer sleeve 170 forms a hollow bore 177b that axially aligns with bore 177a in head portion 171 when the head portion and body portion are connected to one another. Head portion 171 further includes a tool opening 171a for receiving a torque-applying instrument.

As in the embodiments described above, outer sleeve 170 is secured to a pedicle screw by the locking sleeve 180. Locking sleeve 180 has a proximal mounting end 182, a distal mounting end 184 and a flange 183 that extends radially outwardly from the locking sleeve between the tool engaging end and mounting end. Bore 177b has a diameter generally equal to the outer diameter of flange 183. In this arrangement, the outer perimeter of flange 183 frictionally engages the inner wall of bore 177b when the locking sleeve 180 is inserted in the outer sleeve 170. The engagement between the flange 183 and bore 177b maintains the locking sleeve 180 in coaxial alignment with the outer sleeve 170.

Figure 10:
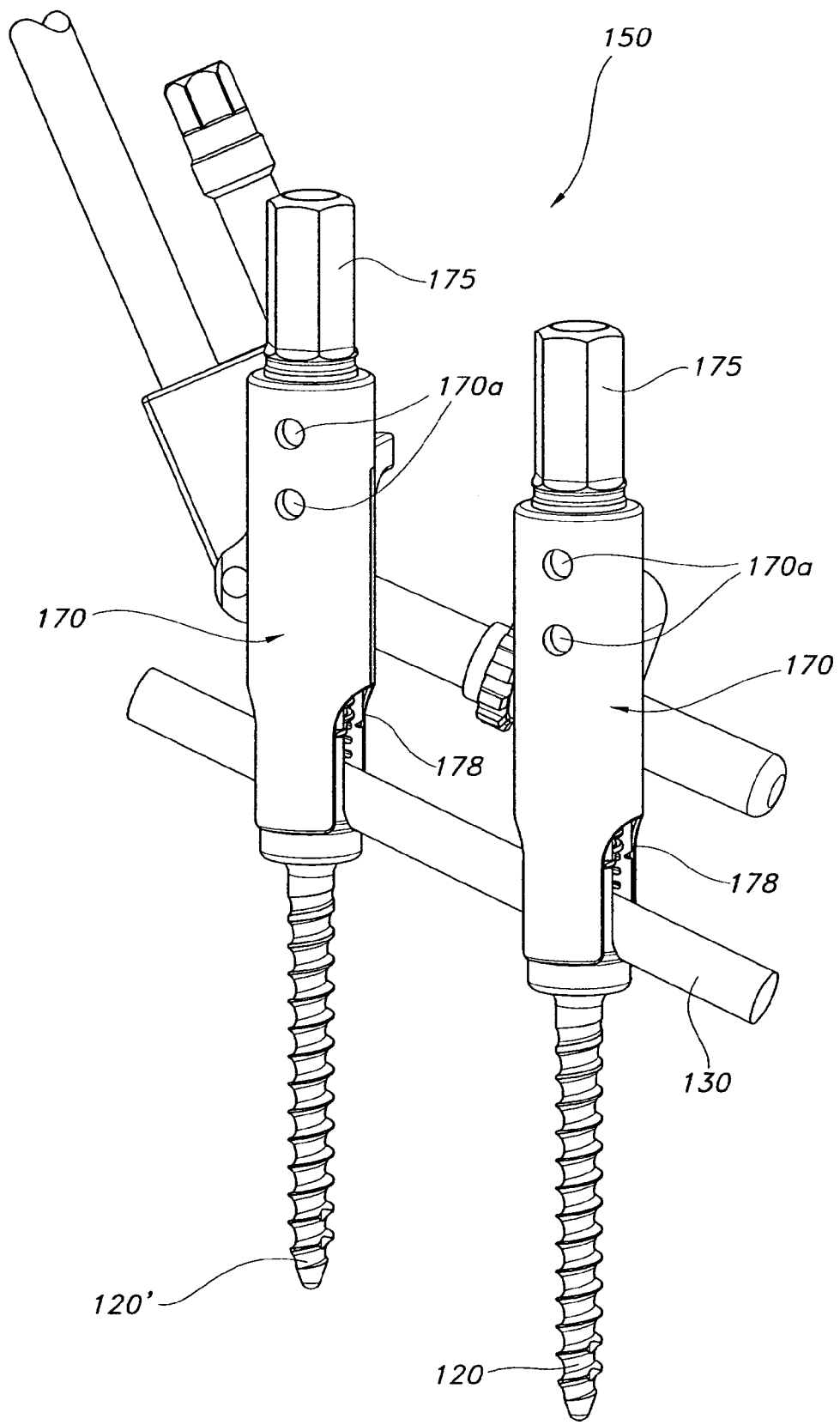
FIG. 10 is a partially-truncated perspective view of the apparatus shown in FIG. 7, showing the apparatus from a different angle of perspective.

The jig apparatus 150 permits fluid access to all areas and parts of the apparatus for purposes of sterilization during manufacture. In the preferred embodiment, the jig apparatus includes one or more openings, slits, notches or similar fluid conduits to allow sterilizing fluid vapors to rapidly reach all inner surfaces during sterilization within about 4 minutes or less. Referring now to FIG. 10, jig assembly 150 includes a pair of side portals 170a extending through the outer sleeve 170 and into the bore 177b. The side portals 170a, notches 178 and tool opening 171a provide rapid fluid communication with interior surfaces in the jig apparatus 150 during the sterilization process. Side portals 171 are positioned approximately midway between the notches 178 and the tool opening 171a so that inner surfaces at the mid portion of the engagement member 161 are sterilized rapidly.

Referring now to FIGS. 11-15, an engagement assembly 260 in accordance with a third embodiment of the invention is shown. Engagement assembly 260 includes a one-piece outer sleeve 270 and a locking sleeve 280. Engagement assembly 260 permits locking sleeve 280 and a set screw 240 to be driven into a screw cap simultaneously with a single torque-applying instrument. Because the engagement assembly 260 has a one-piece outer sleeve, the assembly has fewer components to assemble during the manufacturing process.

Outer sleeve 270 includes a hex head portion 275 and a cylindrical wall 276 that is integrally connected with the hex head portion. Hex head 275 and wall 276 are hollow and form a bore 277 that extends along the longitudinal axis of the outer sleeve 270. Hex head 275 includes a tool-receiving opening 274 adapted to receive a torque-applying tool, and cylindrical wall 276 has a socket end 272 configured to fit over a pedicle screw cap 222, similar to the other embodiments described herein.

Outer sleeve 270 is adapted to receive the locking sleeve 280 within bore 277. Locking sleeve 280 includes a tool engaging end 282 and a mounting end 284. The mounting end 284 includes a locking surface 288 for mounting the engagement assembly 260 onto a screw cap. In FIG. 11, for example, the locking surface 288 is shown as an external thread 289 adapted to engage an internal thread 228 in passage 227 of screw cap 222. The outer surface of locking sleeve 280 forms a circumferential groove 280a that extends around the outer diameter of the locking sleeve. Groove 280a contains a locking ring 283 held in an axially-fixed position on the exterior midportion of the locking sleeve, between tool engaging end 282 and mounting end 284.

Outer sleeve 270 includes an annular groove 279 in the cylindrical wall 276 having an axial width generally equal to the axial width of locking ring 283. In this arrangement, annular groove 279 is adapted to receive locking ring 283 to secure the locking sleeve 280 in a fixed axial position in the outer sleeve 270. Locking ring 283 is fixed with respect to the locking sleeve 280 but slidably displaceable in groove 279. This permits the locking sleeve 280 to rotate in the fixed axial position in the outer sleeve 270. Locking ring 283 is preferably formed of a semi-rigid, resilient material that deflects as the locking sleeve 280 is advanced into the bore 277 of the outer sleeve 270. The resilient material of locking ring 283 biases the locking ring to a position that extends radially outwardly. When the locking sleeve 280 reaches a position in bore 277 where locking ring 283 aligns with annular groove 279, the resilience of the locking ring snaps the ring outwardly and into the annular groove.

The hex head 275 functions somewhat differently from the hex head components in other embodiments of the invention. In the engagement assembly 260, hex head 275 is integrally attached to the cylindrical wall 276. Locking sleeve 280 is separate from the hex head 275 and is free to rotate independently of the hex head. In this arrangement, hex head 275 is operable to hold the outer sleeve 270 in a fixed orientation while the locking sleeve 280 and/or hex nut 240 is rotated.

Figure 13:
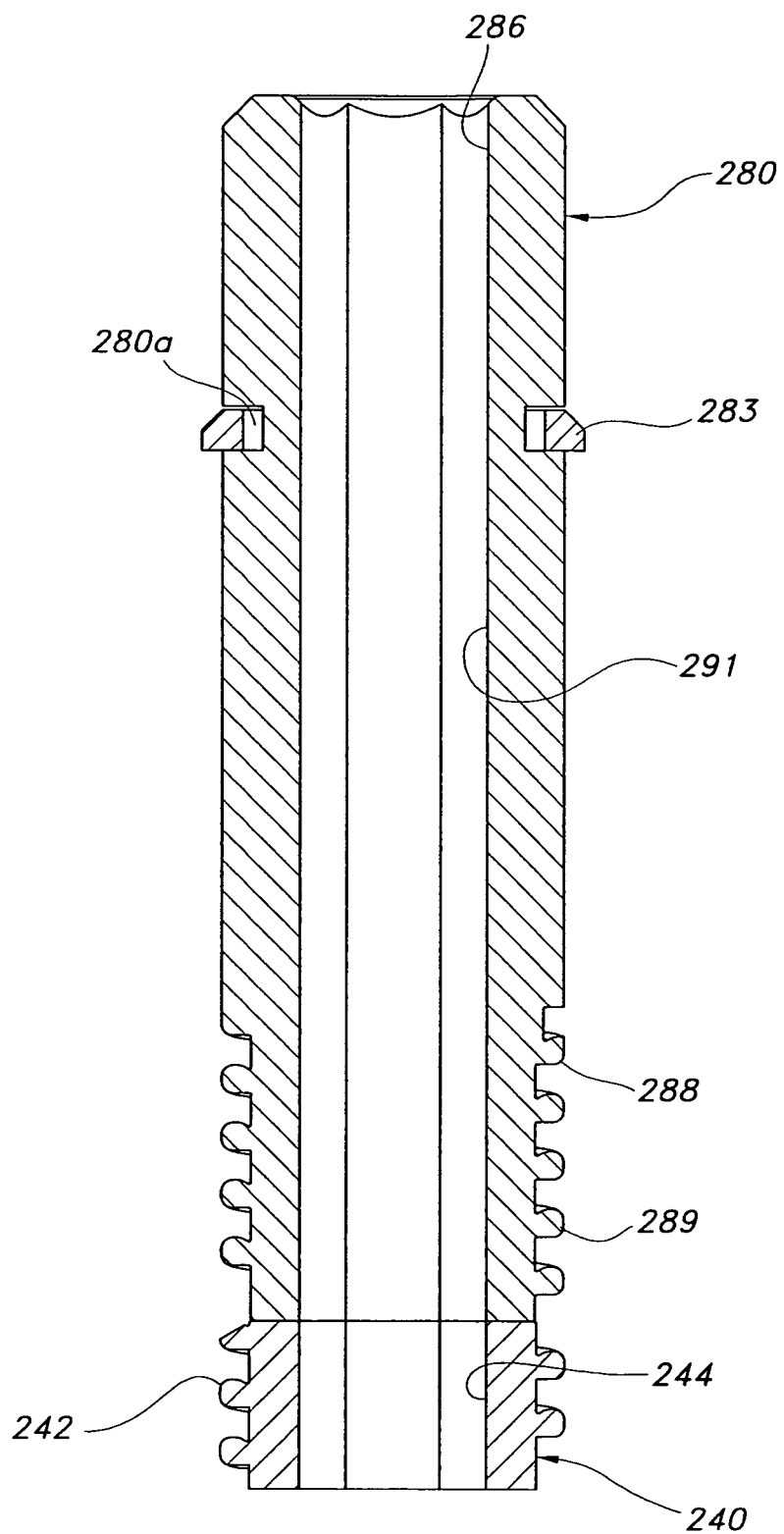
FIG. 13 is a cross-sectional view of a component of the engagement assembly of FIG. 11 in conjunction with a fastener component.
Figure 14:
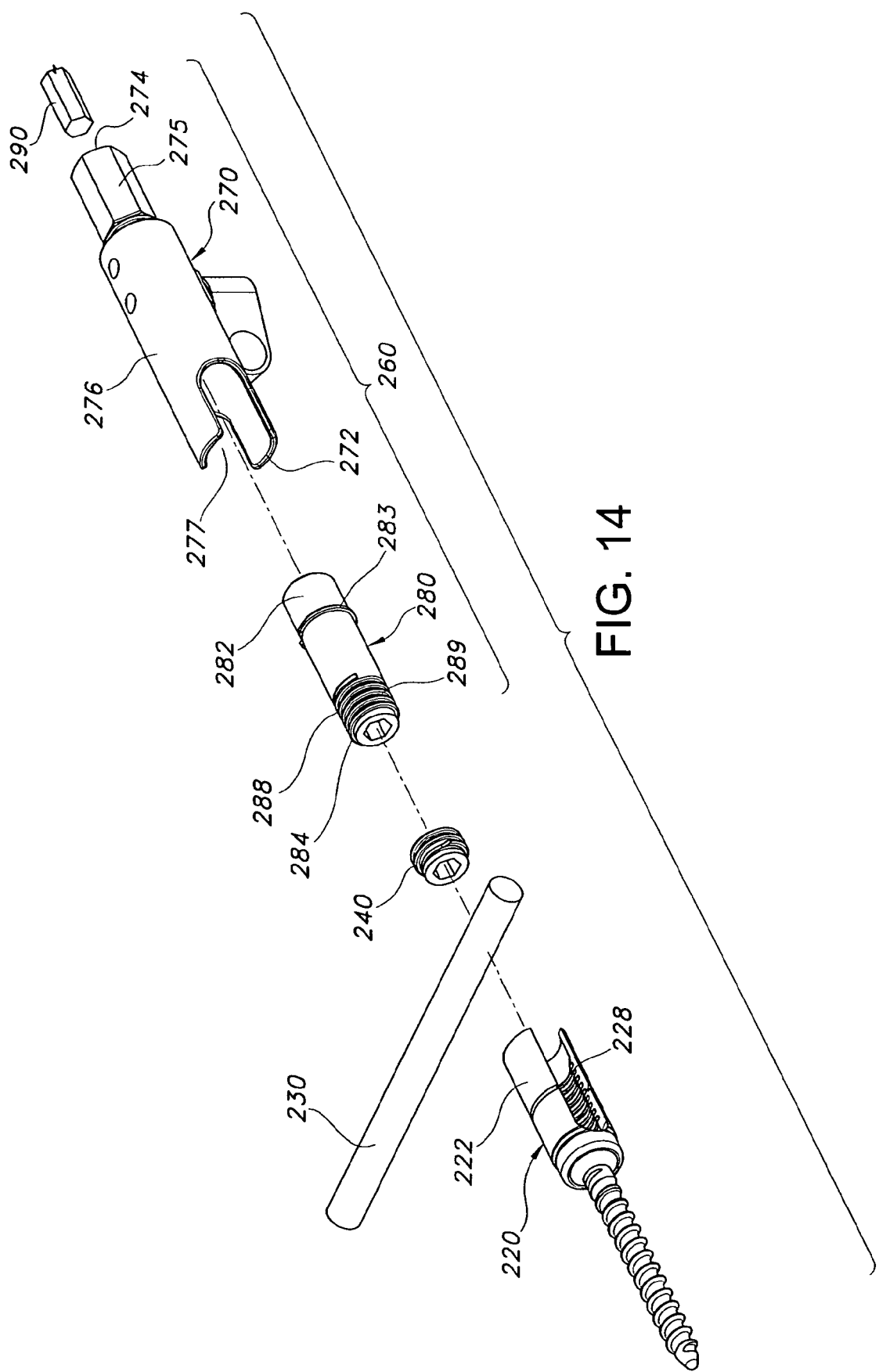
FIG. 14 is an exploded perspective view of components used with the engagement assembly of FIG. 11 shown in a disassembled condition, along with a spine rod and torque-applying tool in accordance with the present invention.
Figure 15:
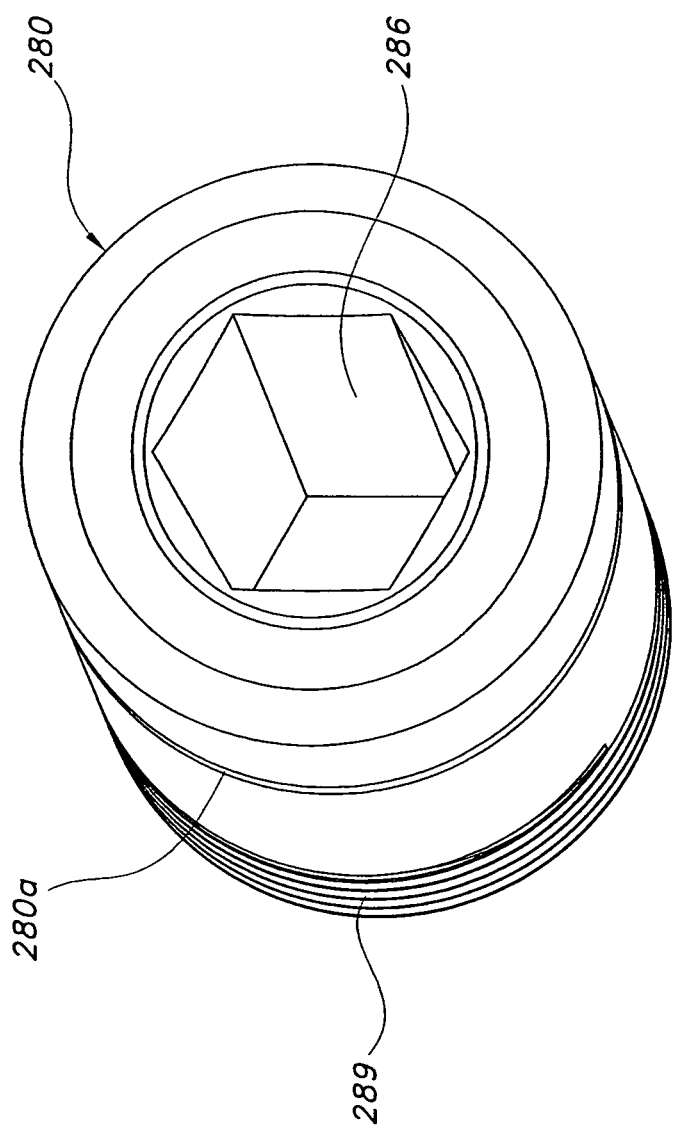
FIG. 15 is a perspective view of a component of the engagement assembly of FIG. 11.

As in other embodiments, engagement assembly 260 can be used with a number of different fasteners to secure a rod in position within a pedicle screw cap. Referring now to FIGS. 13 and 14, the assembly 260 is cooperable with a hex nut 240 to anchor a spinal rod into a pedicle screw cap. In a preferred embodiment, hex nut 240 has internal and external configurations that are identical to the internal and external configurations of locking sleeve 280. In FIG. 13, for example, hex nut 240 has an external thread 242 that is identical to an external thread 289 on the locking sleeve 280. In addition, hex nut 240 has a hexagonal-shaped hole 244, and locking sleeve 280 has a hexagonal-shaped bore 286 having an identical shape and size as the hole in the hex nut. This arrangement permits the hex hole 244 of hex nut 240 and bore 286 of locking sleeve 280 to be axially and radially aligned so that the walls outlining the hex hole and bore form a continuous hexagonal channel 291.

The engagement assembly 260 may be operated to secure a jig assembly over an implanted pedicle screw and spinal rod in the following manner. A spinal rod 230 is initially inserted through the slots of the pedicle screw cap. A torque-applying tool is then used to drive a fastener, such as hex nut 240, into the threaded passage of the pedicle screw cap over the rod. Hex nut 240 is partially driven into the passage to trap the rod within the screw cap, but not completely tightened in the passage. Outer sleeve 270 of engagement assembly 260 is then placed over the pedicle screw cap and rod. Engagement assembly 260 is lowered onto the screw cap such that locking sleeve 280 enters the threaded inner passage of the screw cap. The external thread 289 on locking sleeve 280 engages the inner thread 228 in the screw cap 222 as the engagement assembly 260 is pressed downwardly onto the screw cap. At this point, the notches 278 in outer sleeve 270 are aligned with the slots 226 in the screw cap 222 to enclose the rod in a pair of apertures, similar to the embodiment previously described in connection with FIG. 10.

To tighten down the engagement assembly 260, an Allen wrench 290 or other torque-applying tool is inserted into tool-receiving opening 274, through hex head 275 and into bore 286 of locking sleeve 280. The end of the Allen wrench is advanced partially but not completely through bore 286 of locking sleeve 280, so that the Allen wrench remains out of engagement with the hex nut 240. The Allen wrench is then rotated to axially advance the locking sleeve 280 downwardly into the passage of the screw cap. As the locking sleeve 280 advances axially into the passage of the screw cap, locking ring 283 exerts a downward force on the walls of annular groove 279, tightening down the outer sleeve 270 onto the screw cap. Locking sleeve 280 may be advanced into the passage of the screw cap until the distal end of the locking sleeve abuts the hex nut 240. At this stage, the engagement assembly 260 is secured over the pedicle screw, while the hex nut 240 is in a somewhat loosened condition. This loosened arrangement allows the position of the rod to be incrementally adjusted with the engagement assembly 260, while the jig 250 remains securely mounted to the pedicle screw.

Once the position of the vertebra and rod are set to a desired position, the Allen wrench 290 may be advanced further down into the hex nut 240 to secure the position of the rod 230. As noted above, the bore 286 of locking sleeve 280 has an identical shape and size as the hole 244 in the hex nut 240. Locking sleeve 280 is rotatable to align the walls of the bore 286 with the walls of the hole 244 in hex nut 240 to form a continuous hexagonal channel 291 to receive the Allen wrench. The Allen wrench is advanced into the hex hole 244 and rotated to rotate both the hex nut 240 and the locking sleeve 280. As a result, the locking sleeve 280 and hex nut 240 can be tightened simultaneously with the use of a single tool. The hex nut 240 is rotated to tighten the position of the rod within the screw cap, while the locking sleeve is rotated to further tighten the engagement assembly 260 on the pedicle screw cap.

Once the hex nut 240 is securely tightened against the rod, the distal end of the Allen wrench is pulled out of the hex nut and left within the bore 286 of locking sleeve 280. The Allen wrench is then rotated, preferably in a counterclockwise direction, to withdraw the locking sleeve 280 from the passage 227 of screw cap 222. This releases the engagement assembly 260 from the pedicle screw cap. The jig 250 may then be lifted off of the pedicle screw cap.

As with other embodiments of the present invention, engagement assembly 260 includes a mechanism for applying a counter-torque. In this embodiment, the counter-torque is applied to outer sleeve 270 during rotation and advancement of the locking sleeve 280 and/or hex nut 240. Hex head 275 has an outer perimeter that cooperates with a counter-torque wrench, such as socket wrench 95 shown in FIG. 6. Counter-torque is applied to the hex head 275 to substantially limit or prevent the outer sleeve from rotating in a clockwise direction as the locking sleeve 280 and/or hex nut 240 is rotated in a clockwise direction with the Allen wrench. Without this counter-torque, the torque applied to the locking sleeve 280 and/or hex nut 240 can transfer to the outer sleeve 270, causing the outer sleeve to rotate relative to the screw cap and rod.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An assembly for treating a spinal disorder, the assembly comprising:
   first and second bone fixation screws;
   first and second bone fixation screw caps circumscribing an end of the corresponding one of the first and second bone fixation screw;
   an elongated fixation member extending between the first and second bone fixation screws;
   a fastener encompassed by the corresponding one of the first and second bone fixation screw cap, wherein the elongated fixation member is disposed directly between the fastener and the end of the corresponding one of the first and second bone fixation screw; and
   an adjustment device which translates and rotates a position of the second bone fixation screw cap relative to the first bone fixation screw cap with respect to at least two axes, the adjustment device includes a first engagement member which engages the first bone fixation screw cap and a second engagement member which engages the second bone fixation screw cap, the first and second engagement members being connected to each other by a strut operably connected to an adjusting arm that is displaceable between a locked position and an unlocked position, the first engagement member having a curved stop,
   wherein the adjusting arm directly engages and travels along an outer surface of the curved stop to translate and rotate the second bone fixation screw cap relative to the first bone fixation screw cap about a hinge point defined on a sleeve operably connecting the adjusting arm to the strut.

2. The assembly of claim 1, further comprising a bearing sleeve pivotally connected to the second engagement member, wherein the strut extends through a bore defined in the bearing sleeve.

3. The assembly of claim 2, further comprising an immobilizing mechanism circumscribing the strut and which is axially displaceable on the strut, the immobilizing mechanism being spaced apart from the bearing sleeve when in an unlocked position and abuts against the bearing sleeve when in a locked position.

4. The assembly of claim 1, further comprising:
   an outer sleeve provided about each of the first and second bone fixation screws, each outer sleeve having a socket end, a tool-receiving end and a wall extending between the socket end and tool-receiving end, the socket end having a socket opening which receives the corresponding one of the first and second bone fixation screw cap therein, the outer sleeve wall forming a hollow bore extending between the tool-receiving end and the socket end of the outer sleeve;
   a locking sleeve disposed in each of the outer sleeves, each locking sleeve comprising a proximal end, a distal end and a tool receiving passage extending through the locking sleeve, the distal end of the locking sleeve having an external thread and a flange extending radially outwardly from the locking sleeve, wherein the external thread of the locking sleeve engages an internal thread of the corresponding one of the first and second bone fixation screw cap and the flange of the locking sleeve having an abutment surface which engages a proximal end of the corresponding one of the first and second bone fixation screw cap.

5. The assembly of claim 4, wherein at least one of the fastener and the locking sleeve is axially displaceable within the corresponding one of the first and second bone fixation screw cap.

6. The assembly of claim 5, wherein an outer diameter of the corresponding one of the first and second bone fixation screw cap is less than an inner diameter of the hollow bore of the outer sleeve wall, and wherein an inner wall of the outer sleeve frictionally engages an outer wall of the corresponding one of the first and second bone fixation screw cap.

7. The assembly of claim 4, wherein the corresponding one of the first and second bone fixation screw cap further comprises a pair of slots defined therein, the pair of slots being aligned with a pair of notches defined in the outer sleeve to form an aperture which receives the elongated fixation member therein.

8. The assembly of claim 7, wherein the aperture is elongated with a length longer than a diameter of the elongated fixation member.

9. The assembly of claim 7, wherein the aperture is bounded at a first end by a rounded end of each slot defined in the bone fixation screw cap and bounded at a second end by a rounded end of each notch defined in the outer sleeve.

10. The assembly of claim 4, wherein an outer diameter of the flange is equal to a diameter of the hollow bore of the outer sleeve, wherein the flange frictionally engages an inner surface of the outer sleeve wall which forms the hollow bore.

11. The assembly of claim 4, wherein an inner surface of the outer sleeve, which defines the hollow bore, comprises an annular groove and an outer surface of the locking sleeve comprises a locking ring contained within the annular groove.

12. The assembly of claim 11, wherein the locking sleeve is rotatable in a fixed axial position relative to the outer sleeve.

13. The assembly of claim 11, wherein an outer surface of the locking sleeve includes a circumferential groove defined therein, the locking ring being contained in the circumferential groove.

14. The assembly of claim 11, wherein an axial width of the annular groove is equal to an axial width of the locking ring.

15. The assembly of claim 11, wherein the locking ring is formed of a semi-rigid, resilient material.

16. The assembly of claim 4, wherein the outer sleeve further comprises a head portion and a body portion connected to the head portion.

17. The assembly of claim 16, wherein the head portion includes a hex head and a collar circumscribing the hex head.

18. The assembly of claim 17, wherein a distal end of the hex head is connected to the proximal end of the locking sleeve.

19. The assembly of claim 18, wherein the hex head of the outer sleeve and the proximal end of the locking sleeve are integrally connected.

20. The assembly of claim 16, wherein the head portion and the body portion are integrally connected, and wherein the outer sleeve is a one-piece component.

21. The assembly of claim 1, wherein the corresponding one of the first and second bone fixation screw cap comprises a threaded internal passage, and an outer surface of the fastener is threaded and engages the threaded internal passage of the corresponding one of the first and second bone fixation screw cap.

22. The assembly of claim 1, wherein the adjusting arm passes through a bore defined in the sleeve.

23. The assembly of claim 22, wherein the adjusting arm threadably engages threads defined in the bore of the sleeve.

* * * * *